(12) United States Patent
Ban

(10) Patent No.: US 6,382,796 B1
(45) Date of Patent: May 7, 2002

(54) CORNEAL SHAPE MEASURING APPARATUS

(75) Inventor: Yukinobu Ban, Aichi (JP)

(73) Assignee: Nidek Co., Ltd., Aichi (JP)

( * ) Notice: Subject to any disclaimer, the term of this patent is extended or adjusted under 35 U.S.C. 154(b) by 159 days.

(21) Appl. No.: 09/587,511

(22) Filed: Jun. 5, 2000

(30) Foreign Application Priority Data

Jun. 4, 1999 (JP) ............................ 11-157265

(51) Int. Cl.[7] .................................................. A61B 3/10
(52) U.S. Cl. ........................................................ 351/212
(58) Field of Search ................................. 351/205, 206, 351/211, 212, 221, 246; 606/4, 5

(56) References Cited

U.S. PATENT DOCUMENTS

| | | | |
|---|---|---|---|
| 5,500,697 A | 3/1996 | Fujieda | 351/212 |
| 5,684,562 A | 11/1997 | Fujieda | 351/212 |
| 5,694,197 A | * 12/1997 | Tsukada et al. | 351/212 |
| 5,907,388 A | 5/1999 | Fujieda | 351/211 |

FOREIGN PATENT DOCUMENTS

| | | | |
|---|---|---|---|
| JP | 7-124113 | 5/1995 | A61B/3/10 |
| JP | 8-164113 | 6/1996 | A61B/3/10 |
| JP | 10-108836 | 4/1998 | A61B/3/10 |
| JP | 10-108837 | 4/1998 | A61B/3/10 |

* cited by examiner

*Primary Examiner*—George Manuel
(74) *Attorney, Agent, or Firm*—Sughrue Mion, PLLC

(57) ABSTRACT

A corneal shape measuring apparatus for measuring a corneal shape of an eye to be examined, includes: an index projecting section having a first projecting optical system for projecting a corneal shape measuring index onto a cornea of the eye; an index detecting section having a first imaging optical system for obtaining an image of an anterior eye segment including an image of the measuring index formed on the cornea; an arithmetic section for obtaining the corneal shape based on the obtained image of the measuring index; and an input section for inputting, to the arithmetic section, information on a boundary position between a pupil and an iris of the eye. The arithmetic section corrects information on the image of the measuring index based on the information on the boundary position thus inputted, and obtains the corneal shape based on the thus corrected information on the image of the measuring index.

15 Claims, 5 Drawing Sheets

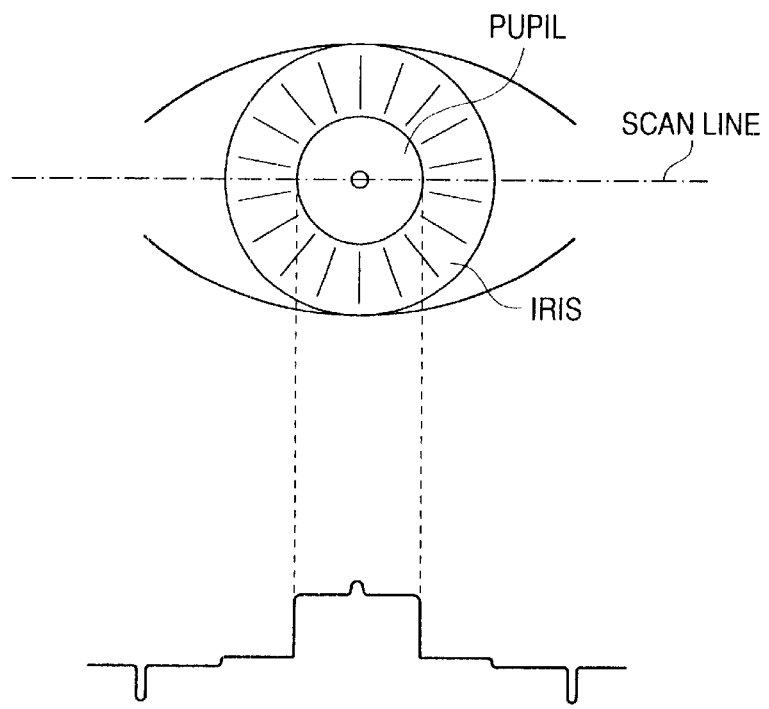
FIG. 3 (a)
FIG. 3 (b)
FIG. 3 (c)
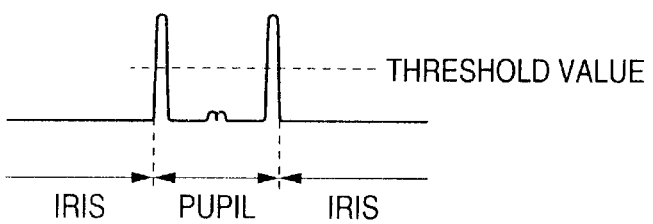
FIG. 3 (d)

CORNEAL SHAPE MEASURING APPARATUS

BACKGROUND OF THE INVENTION

The present invention relates to a corneal-shape measuring apparatus for measuring the shape of a cornea of an eye to be examined.

As an apparatus for measuring a corneal shape, a corneal topography apparatus for measuring the corneal curvature at a multiplicity of regions of the cornea and displaying its distribution as topography is known. In this apparatus, a measurement index of a predetermined pattern, such as a Placido ring, is projected onto the cornea of the eye to be examined, and its reflected image of the cornea (Placido ring image or the like) is photographed by a CCD camera or the like. Then, by subjecting the photographed image to image analysis, the curvature distribution in a substantially entire region of the cornea is determined, and is graphically displayed on a display.

However, in the image of the anterior eye segment including the cornea onto which the measurement index (Placido ring) has been projected, there is a difference in luminance (the quantity of light; hereinafter the same) between a pupil portion and an iris portion, so that it is difficult to discern the change of luminance in the image of the measurement index in the vicinity of a boundary between the pupil and the iris. Namely, as can be seen from a graph shown in FIG. 4 indicating the change of luminance on a straight line passing the center of the Placido ring image, since the iris region is photographed such that the luminance of the light reflected by the iris is added to the change of luminance of the Placido ring image, it is difficult to detect the edge of the Placido ring image. Hence, the measurement accuracy is lowered.

As an corneal-shape measuring apparatus incorporating an objective occular-refractive-power measuring mechanism in which a measurement index of slit light or the like is projected onto the fundus of the eye to be examined, and the refractive power of the eye is obtained by detecting the index image reflected from the fundus, there is a type in which a index (Placido ring or the like) for measuring the corneal shape is projected with red to infrared light so as to avoid the effect of the miosis of the eye to be measured on the measurement of the refractive power. However, since the red to infrared light is reflected well by the iris, it is even more difficult to discern the change of luminance in the image of the measurement index in the vicinity of the boundary between the pupil and the iris. Hence, it is very difficult to detect the edge of the index image.

SUMMARY OF THE INVENTION

The object of the invention is to provide a corneal-shape measuring apparatus which is capable of suppressing the effect due to the light reflected from the iris and of measuring the corneal shape with high accuracy.

To overcome the above-described problems, the invention is characterized by having the following features:

(1) A corneal shape measuring apparatus for measuring a corneal shape of an eye to be examined, the apparatus comprising:
index projecting means having a first projecting optical system for projecting a corneal shape measuring index onto a cornea of the eye;
index detecting means having a first imaging optical system for obtaining an image of an anterior eye segment including an image of the measuring index formed on the cornea;
arithmetic means for obtaining the corneal shape based on the obtained image of the measuring index; and
input means for inputting, to the arithmetic means, information on a boundary position between a pupil and an iris of the eye,
wherein the arithmetic means corrects information on the image of the measuring index based on the information on the boundary position thus inputted, and obtains the corneal shape based on the thus corrected information on the image of the measuring index.

(2) The apparatus of (1), further comprising:
diaphanoscopic image obtaining means having an illuminating optical system for projecting a light onto a fundus of the eye, and illuminating the anterior eye segment with the light reflected from the fundus, and a second imaging optical system for obtaining a diaphanoscopic image of the anterior eye segment; and
boundary position detecting means for detecting the boundary position between the pupil and the iris based on the diaphanoscopic image thus obtained,
wherein the input means inputs information on the thus detected boundary position to the arithmetic means.

(3) The apparatus of (2), wherein the second imaging optical system is used commonly as the first imaging optical system.

(4) The apparatus of (2), further comprising:
occular refractive power measuring means having a second projecting optical system for projecting a light onto the fundus of the eye, and light receiving optical system for receiving the light reflected from the fundus of the eye,
wherein the illuminating optical system is used commonly as the second projecting optical system.

(5) The apparatus of (1), wherein the arithmetic means divides luminance information on the image of the measuring index into a pupil region and an iris region based on the inputted boundary position information, obtains a luminance difference between the pupil region and the iris region, remove reflected light component of the iris region based on the thus obtained luminance difference to correct the luminance information on the image of the measuring index, and obtains the corneal shape based on the thus corrected luminance information.

(6) The apparatus of (1), further comprising:
displaying means for displaying the image of the anterior eye segment thus obtained,
wherein the input means inputs the boundary position between the pupil and the iris based on a display by the displaying means.

(7) The apparatus of (1), wherein the index projecting means includes means for projecting, as the measuring index, a ring pattern index onto the cornea, and the arithmetic means detects an edge position of the obtained ring pattern index, and obtains a corneal curvature based on the detected edge position.

(8) The apparatus of (7), wherein the first projecting optical system provided in the index projecting means includes:
a Placid plate in which light transmitting portions and light shielding portions are alternately arranged substantially concentrically; and
a plurality of light sources for illuminating the Placid plate.

(9) The apparatus of (8), wherein the light sources emits a light whose wavelength falls within red to infrared region.

(10) A corneal shape measuring apparatus for measuring a corneal shape of an eye to be examined, the apparatus comprising:
image input means for inputting an image of an anterior eye segment including a corneal shape measuring index image formed on a cornea;
arithmetic means for obtaining the corneal shape based on the inputted measuring index image;
boundary position input means for inputting, to the arithmetic means, information on a boundary position between a pupil and an iris of the eye,
wherein the arithmetic means corrects information on the measuring index image based on the inputted information on the boundary position, and obtains the corneal shape based on the corrected information on the measuring index image.

(11) The apparatus of (10), further comprising:
diaphanoscopic image obtaining means having an illuminating optical system for projecting a light onto a fundus of the eye, and illuminating the anterior eye segment with the light reflected from the fundus, and an imaging optical system for obtaining a diaphanoscopic image of the anterior eye segment; and
boundary position detecting means for detecting the boundary position between the pupil and the iris based on the diaphanoscopic image thus obtained,
wherein the boundary position input means inputs information on the thus detected boundary position to the arithmetic means.

(12) The apparatus of (11), further comprising:
ocular refractive power measuring means having a projecting optical system for projecting a light onto the fundus of the eye, and a light receiving optical system for receiving the light reflected from the fundus of the eye,
wherein the illuminating optical system is used commonly as the projecting optical system.

(13) The apparatus of (10), wherein the arithmetic means divides luminance information on the measuring index image into a pupil region and an iris region based on the inputted boundary position information, obtains a luminance difference between the pupil region and the iris region, remove reflected light component of the iris region based on the thus obtained luminance difference to correct the luminance information on the measuring index image, and obtains the corneal shape based on the thus corrected luminance information.

(14) The apparatus of (10), further comprising:
displaying means for displaying the obtained image of the anterior eye segment,
wherein the boundary position input means inputs the boundary position between the pupil and iris based on a display by the displaying means.

(15) The apparatus of (10), wherein the image input means inputs the image of the anterior eye segment in which an image of a ring pattern index is formed as the measuring index on the cornea, and arithmetic means detects an edge position of the inputted image of the ring pattern index, and obtains a corneal curvature based on the detected edge position.

The present disclosure relates to the subject matter contained in Japanese patent application No. Hei. 11-157265 (filed on Jun. 4, 1999), which is expressly incorporated herein by reference in its entirety.

BRIEF DESCRIPTION OF THE DRAWINGS

FIG. 3 is an explanatory diagram of a method for detecting the position of a boundary between the pupil and the iris from a diaphanoscopic image (retro-illumination image);

DESCRIPTION OF THE PREFERRED EMBODIMENT

Figure 1:
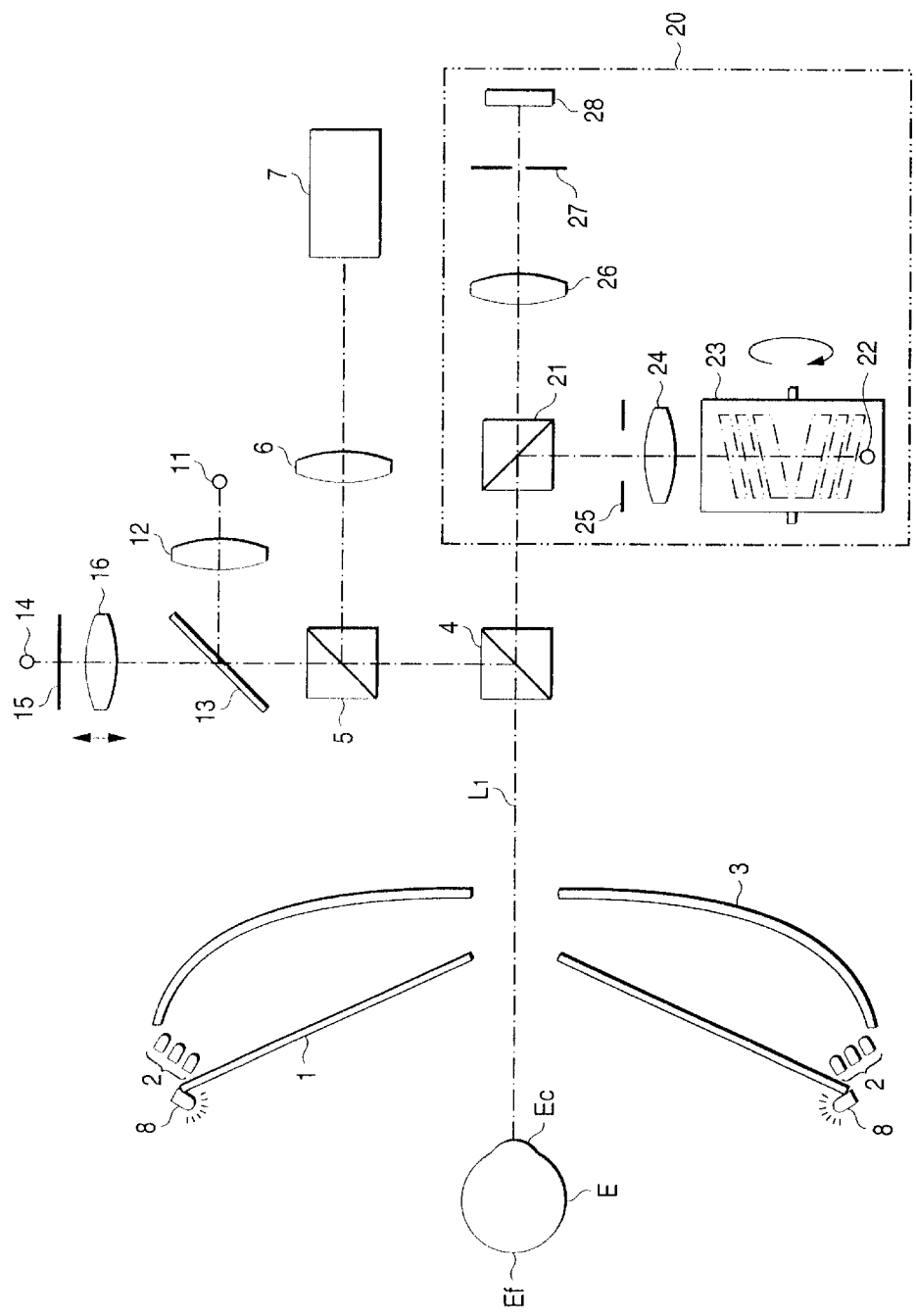
FIG. 1 is a schematic diagram of essential portions of an optical system of a corneal-shape measuring apparatus in accordance with an embodiment.

Referring now to the drawings, a description will be given of an embodiment of the invention. FIG. 1 is a schematic diagram of essential portions of an optical system of a corneal-shape measuring apparatus in accordance with the invention.

Reference numeral 1 denotes a Placido plate which is formed by a diffusing plate having an aperture portion in its center, and the Placido plate 1 has a multiplicity of annular light-transmitting portions and light-shielding portions which are formed alternately concentrically around a photographing optical axis $L_1$. A reflecting plate 3 is provided in the rear of the Placido plate 1, and reflects the light in the red to infrared regions emitted from LEDs 2, which are an illuminating light source, so as to substantially uniformly illuminate the Placido plate 1 from the rear. The light transmitted through the light-transmitting portions of the Placido plate 1 is reflected by the cornea $E_c$ of an eye E to be measured, thereby forming a so-called Placido ring image. A beam splitter 4 is disposed on the optical axis $L_1$ in the rear of the Placido plate 1, and an occular-refractive-power measuring optical system 20 is disposed in the rear thereof. The beam of the Placido ring image, after being reflected by the beam splitter 4 and a beam splitter 5, forms an image on an imaging plane of a CCD camera 7 by an image-forming lens 6. The CCD camera 7 is used in the observation of the anterior eye segment, the detection of an alignment index image (bright spot) formed on the cornea $E_c$, the photographing of the Placido ring image formed on the cornea $E_c$, and the photographing of a diaphanoscopic image (retro-illumination image; the same is applied in the following description) of the anterior eye segment.

Reference numeral 8 denotes an anterior eye segment illuminating lamp which is embedded in the Placido plate 1 and emits near infrared light, and this anterior eye segment illuminating lamp 8 is used for observation of the anterior eye segment of the eye E. The anterior eye segment illuminated by the light from the lamp 8 is photographed by the CCD camera 7.

Reference numeral 11 denotes a light source for alignment which emits near infrared light and is disposed in the vicinity of the focusing position of a focusing lens 12. A dichroic mirror 13 has the characteristic of reflecting the near infrared light emitted from the light source 11 and transmitting visible light emitted from a fixation light source 14 which will be described later. The light emitted from the light source 11 is converted to a substantially parallel bundle of rays, is then reflected by the dichroic mirror 13, and is projected onto the eye E through the beam splitters 5 and 4.

This light is reflected by the cornea $E_c$ and forms a corneal reflected image (bright spot). The corneal reflected image (bright spot) passes along a route similar that of the Placido ring image, is photographed by the CCD camera 7, and is used for the alignment between the eye E and the apparatus.

Reference numeral 14 denotes a fixation light source which emits visible light, and uniformly illuminates a fixation target board 15. The fixation target illuminated by the light source 14 is visually recognized by the eye E through a lens 16, the dichroic mirror 13, and the beam splitters 5 and 4. Further, the fogging of the eye E is effected as the lens 16 is moved in the direction of the optical axis.

An occular-refractive-power measuring optical system 20 is comprised of a beam splitter 21, an illuminating light source 22 which emits infrared light, a rotating sector 23, a projecting lens 24, a diaphragm 25, a light receiving lens 26, a diaphragm 27, and a light receiving unit 28.

Two kinds of slits extending in a 45-degree direction and a 135-degree direction with respect to the rotating direction of the rotating sector 23 are formed in the rotating sector 23. The slits are illuminated by the light source 22, and the slit beams scanned by the rotation of the rotating sector 23 are focused in the vicinity of the cornea $E_c$ through the lens 24, the diaphragm 25, the beam splitter 21, and the beam splitter 4, and are then projected onto the fundus $E_f$.

The diaphragm 27 is disposed at the position of the rear focal point of the lens 26, and the light receiving unit 28 is disposed at a position substantially conjugative with the cornea $E_c$ with respect to the lens 26. The light receiving unit 28 has two pairs of light receiving elements (i.e., four light receiving elements) which are disposed symmetrically about the optical axis $L_1$. The light receiving elements are disposed at 90-degree intervals with the optical axis $L_1$ as the center, and are arranged so as to be capable of measuring the refractive power with a 2.5 mm pupillary radius. Two kinds of slit beams with different inclinations are projected onto the fundus $E_f$ as the rotating sector 23 rotates. The refractive power of the eye is calculated by a computation control unit 30, which will be described later, on the basis of a phase difference signal obtained by the pairs of light receiving elements when one slit light is scanned and a phase difference signal obtained by the pairs of light receiving elements when the other slit light is scanned.

In addition, the light source 22 has the function of a light source for photographing a diaphanoscopic image. The light emitted from the light source 22, after being temporarily focused in the vicinity of the cornea $E_c$, passes through the pupil, and illuminates the fundus $E_f$ substantially uniformly. This light is irregularly reflected by the fundus $E_f$, and illuminates the anterior eye segment of the eye E from inside. After being reflected by the beam splitters 4 and 5, this light forms an image of the anterior eye segment on the imaging plane of the CCD camera 7 by means of the lens 6, thereby forming a diaphanoscopic image. At this time, since the slits of the rotating sector 23 are rotating at a sufficiently high speed with respect to the imaging by the CCD camera 7, the effect of the slits on the diaphanoscopic image is negligible.

Figure 2:
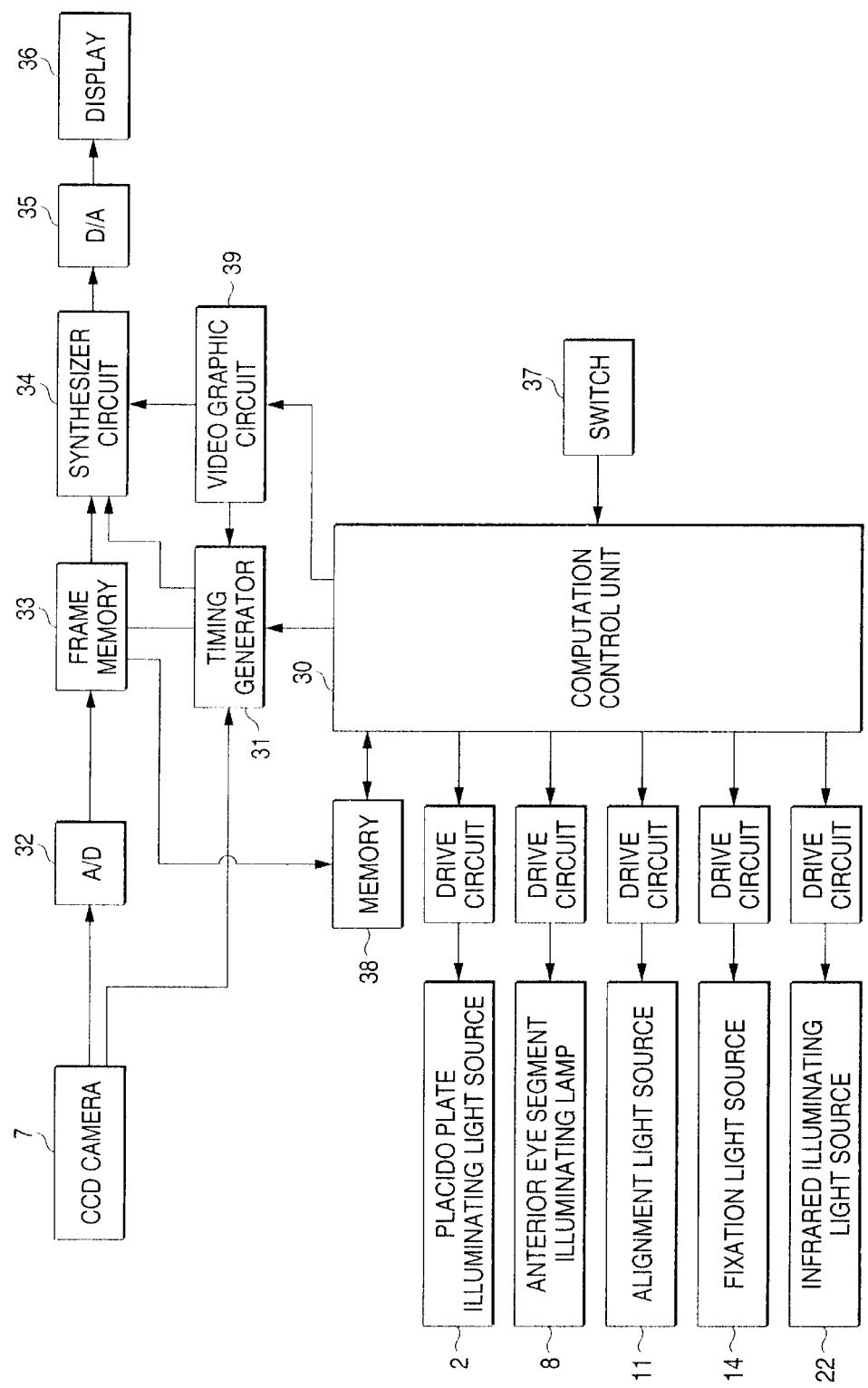
FIG. 2 is a schematic diagram of a control system of the corneal-shape measuring apparatus.

FIG. 2 is a schematic diagram of a control system. An image signal from the CCD camera 7 is digitized by an A/D converter 32, and is fetched into a frame memory 33 in synchronism with a signal from a timing generator 31. The image fetched into the frame memory 33 is displayed on a display 36 virtually in real time through a synthesizer circuit 34 and a D/A converter 35.

When a signal from a switch 37 is inputted to the control unit 30, the control unit 30 causes the image fetched into the frame memory 33 to be stored in another memory 38. Reference numeral 39 denotes a video graphic circuit for generating video graphics and characters, and this video graphic circuit 39 causes video graphics of the distribution of the corneal shape to be displayed on the display 36 or causes a composite image of the image photographed by the CCD camera 7 and characters such as the measurement data to be displayed thereon.

Figure 6:
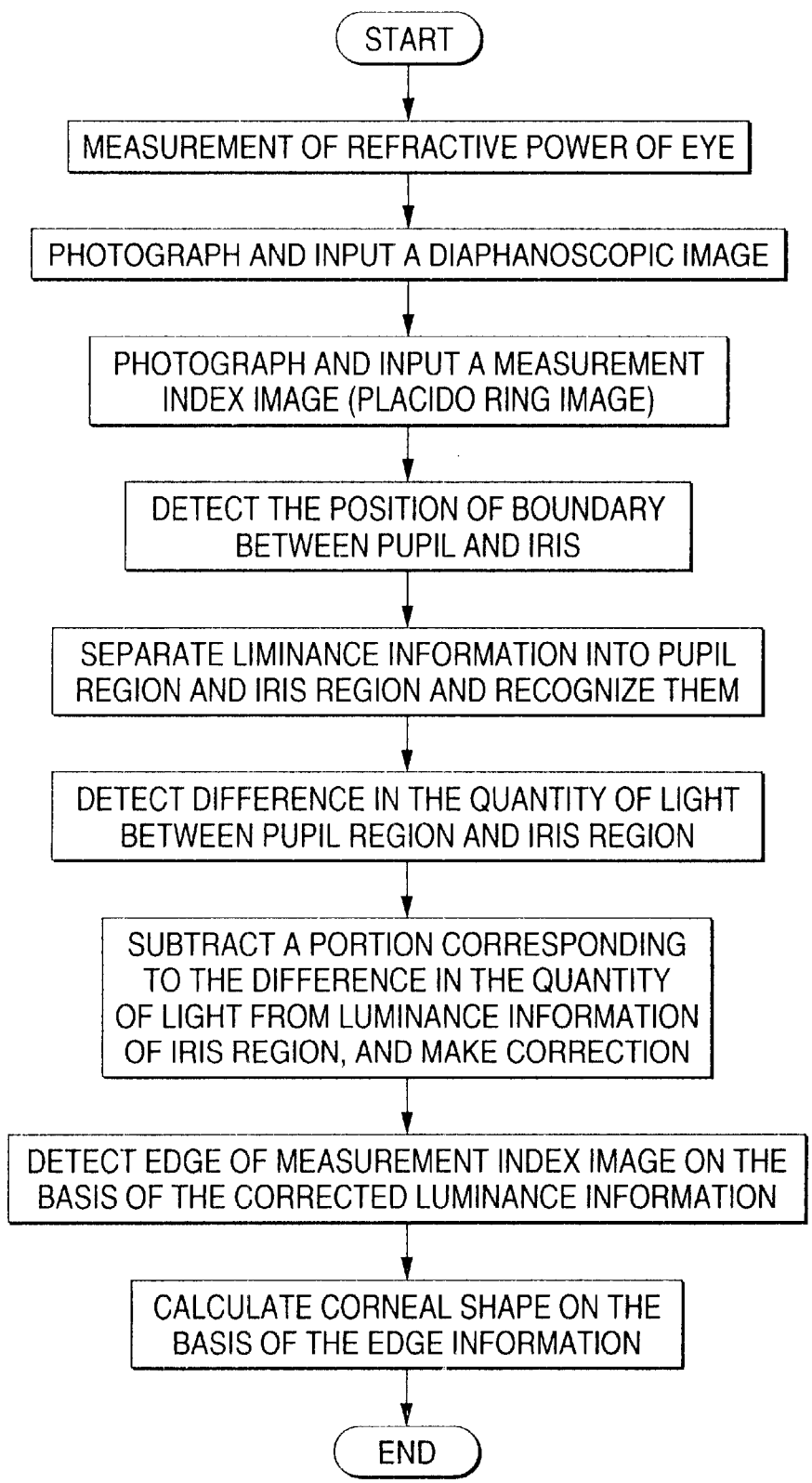
FIG. 6 is a flowchart of measurement of the corneal shape.

Referring to the flowchart shown in FIG. 6, a description will be given of the operation of the apparatus constructed as described above in a case where the measurement of the refractive power of the eye and the measurement of the corneal shape are effected in a continuous measurement mode in which these measurements are effected continuously.

The control unit 30 lights up the lamp 8, the light source 11, and the light source 14. The examiner causes the eye E to be fixated at the fixation target. The image of the anterior eye segment illuminated by the lamp 8 is photographed by the CCD camera 7, and is displayed on the display 36. While viewing the display 36, the examiner moves the measuring section of the apparatus incorporating the optical system with respect to a basal part by means of known sliding mechanism, so as to bring the corneal reflected image (bright spot) based on the light source 11 and an unillustrated reticle mark (generated by the graphic circuit 39) displayed on the display 36 into a predetermined positional relationship.

When the alignment between the eye E and the apparatus is thus completed, if the examiner inputs a signal by pressing the switch 37, the control unit 30 lights up the light source 22, causes the slit light formed by the rotating sector 23 to be projected onto the fundus $E_f$, and moves the lens 16 to effect the fogging of the eye E. Subsequently, the corneal center in the radial (meridian) direction where the light receiving elements are located is determined from output signals from the light receiving elements which change in conjunction with the movement the slit images on the light receiving unit 28. Then, the refractive power at a corneal region corresponding to each light receiving element is determined on the basis of the phase difference of output signals from the respective light receiving elements with respect to that center. It should be noted that, as for the details of the measurement of the refractive power, reference should be made to U.S. Pat. No. 5,907,388 (JP-A-10-108836) (title of the invention: Apparatus for Measuring the Refractive Power of an Eye) filed by the present applicant.

Upon completion of the measurement of the refractive power of the eye, the photographing of a diaphanoscopic image and the measurement of the corneal shape are effected. The diaphanoscopic image of the eye E (anterior eye segment) illuminated by the reflected light from the fundus $E_f$ by means of the light-source 22 is photographed by the CCD camera 7. The diaphanoscopic image captured by the CCD camera 7 is stored in the memory 38 through the frame memory 33.

If the data of the diaphanoscopic image is stored, the control unit 30 lights up the LEDs 2 for a predetermined time duration. A Placido ring image is formed on the cornea $E_c$ by the light which passed through the Placido plate 1. The Placido ring image together with the anterior eye segment image is photographed by the CCD camera 7, and its image data is stored in the memory 38 through the frame memory 33. Upon completion of the photographing of the Placido ring image, the control unit 30 proceeds to computation processing for calculating the pupillary region and the corneal curvature.

To calculate the pupillary region on the basis of the diaphanoscopic image of the eye E, the position of a boundary (edge) between -the pupil (bright portion) and the iris (dark portion) is determined follows (see FIG. 3). To ascertain the position of the edge between the pupil and the iris, a luminance signal waveform (FIG. 3(b)) for each scan line is subjected to differentiation processing. Since the signal waveform (FIG. 3(c)) subjected to the differentiation processing is a positive/negative signal, this signal is converted to a signal of a positive value (FIG. 3(d)) by squaring the signal. Since the luminance (quantity of light) difference is large at the edge position between the pupil and the iris, the squared differential signal exhibits a large value in comparison with other regions, the position of the pixel at the edge portion can be specified by specifying a threshold level. The pupillary region (the edge position between the pupil and the iris) can be obtained by specifying the position of the pixel of the edge portion for each scan line and by storing the same. It should be noted that, as for the details of the edge detection of the pupillary region, reference should be made to U.S. Pat. No. 5,684,562 (JP-A-8-164113) (title of the invention: Opthalmic Apparatus) filed by the present applicant.

Figure 4:
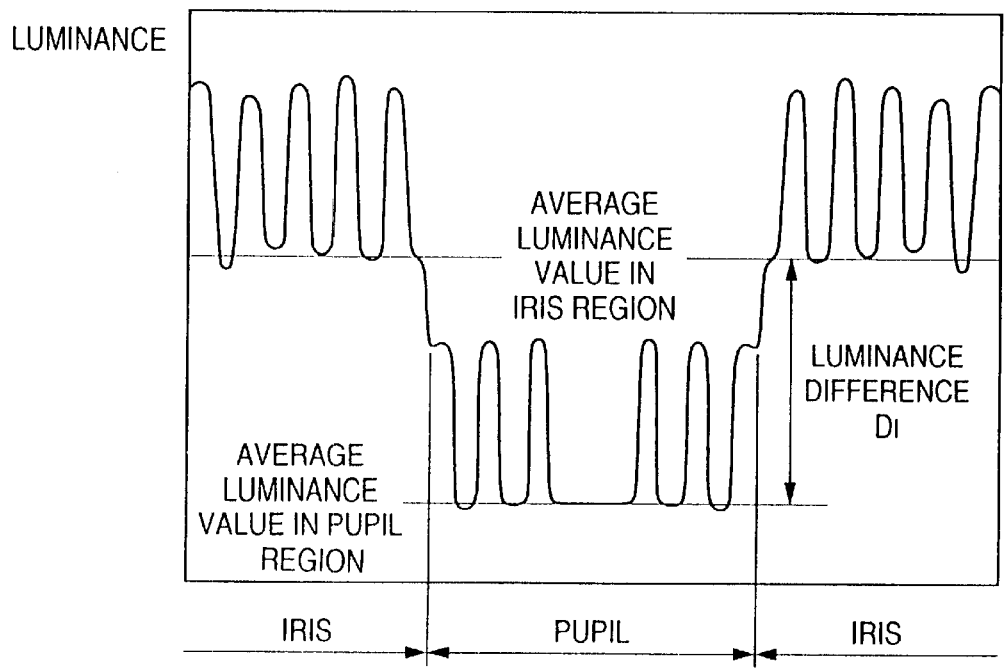
FIG. 4 is a graph on the change of luminance on a straight line passing the center of a Placido ring image.
Figure 5:
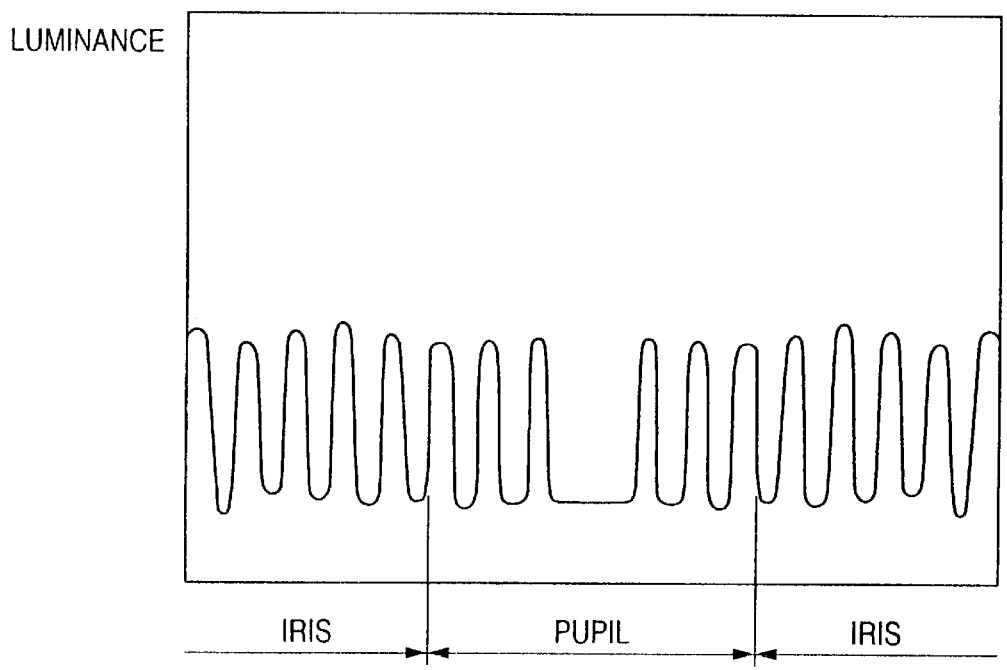
FIG. 5 is a graph on the change of luminance after elimination of an iris reflected light component.

After the pupillary region (the position of the boundary between the pupil and the iris) has been obtained, the control unit 30 corrects the detected information on the Placido ring image, and calculates the corneal shape on the basis of its results. Hereafter, a description will be given of the method of calculating the corneal shape with reference to the graphs on the change of luminance shown in FIGS. 4 and 5.

First, the control unit 30 detects portions with low luminance values corresponding to the light-shielding portions of the Placido plate 1 from the graphs on the change of luminance of the Placido ring image. In the graph on the change of luminance of the Placido ring image, the change of the luminance value is observed as a waveform due to the rings formed by the light-transmitting portions and the light-shielding portions which are alternately arranged. Since the light-shielded portion is the lowest point of each wave of the luminance change, the luminance change graph is traced from one side, and the position of the pixel where the luminance value is smaller than the luminance values of both neighboring pixels is a lowest point. Thus, the pixel positions and luminance values at the lowest points of the waves are consecutively stored.

Next, on the basis of the boundary position information obtained by the detection processing of the pupillary region, the stored lowest points are classified into the pupillary region and the iris region on the basis of their pixel positions, and average values of the luminance values of the respectively classified pixels are calculated. A difference $D_I$ between the average luminance value of the lowest points in the pupillary region and the average luminance value of the lowest points in the iris region is determined.

Subsequently, with respect to the luminance values of the pixels of a portion belonging to the iris region, the difference $D_I$ between the average luminance values is subtracted from each of those luminance values. As a result, the luminance value of the reflected light component at the iris portion is eliminated, and as shown in the graph on the luminance change after elimination of the iris reflected light component, the change of the luminance value in the Placido ring image can be clearly recognized. It should be noted that if the difference $D_I$ between the average luminance values is obtained separately for the left region and the right region of the iris, the biasing of illumination can be eliminated, so that the accuracy improves further.

After the elimination processing of the iris reflected light component, an intermediate value between a maximum luminance value and a minimum luminance value is set as a threshold for each information on luminance (for each wave) of each fringe component of the Placido ring image, and the position of the pixel having luminance information serving as the threshold is detected and stored as the edge position of each fringe component of the Placido ring image. The above-described processing is effected for each radial (meridian) direction at a predetermined angle (e.g., one degree each), thereby obtaining edge positions over the entire circumference.

The control unit 30 determines the corneal curvature on the basis of the detected edge information of the Placido ring image. As for the corneal curvature, central coordinates are calculated from the edge coordinates of an innermost circle of the Placido ring image, and the distance from the central coordinates to each ring edge is calculated for each meridian at a predetermined angle (e.g., one degree each). If the distance from the central coordinates to each ring edge has been obtained for each angle and meridian, these data are subsequently compared with the data which have been obtained and stored from the known curvature spheres, thereby obtaining the corneal curvature at each position. It should be noted that, as for the calculation of the corneal shape (corneal curvature) based on the Placido ring image, since a detailed description is given in U.S. Pat. No. 5,500,697 (JP-A-7-124113) (title of the invention: Ophthalmic Apparatus) filed by the present applicant, reference should be made thereto.

The various data obtained as described above are displayed on the display 36, and the contents of the display can be selected by display switches.

Although, in the above-described embodiment, a description has been given of the operation in which the measurement is effected in the continuous measurement mode, a change over between the occular-refractive-power measurement mode and the corneal-shape measurement mode may be made by a mode changeover switch or the like, and only the respective measurement may be performed. In this case, it suffices if the above-described photographing of the diaphanoscopic image is effected immediately before the photographing of the Placido ring image in interlocking relation to the input of a signal for photographing.

In addition, the determination of the position of the boundary between the pupil and the iris maybe detected by ordinary image processing based on the anterior eye segment image in addition to the photographing of a diaphanoscopic image, or may be effected by consecutively designating boundary positions by an input means such as a mouse with respect to the anterior eye segment image displayed on the monitor.

Further, a program of the method of measuring the corneal shape in accordance with the invention may be stored in a computer, image data such as a photograph of the Placido ring image photographed by another apparatus may be inputted, and the corneal shape may be measured on the basis of the inputted image data.

Furthermore, although in this embodiment a description has been given by citing as an example the Placido ring index as the index for measurement of the corneal shape, the corneal shape can be measured with high accuracy while eliminating the effect of the reflected light from the iris in the case of a fringe index and a spot index as well.

In addition, although in this embodiment an optical system (the light source 22 and the like) for measurement of the refractive power of the eye and an optical system (the CCD camera 7 and the like) for photographing a Placido ring image are used for photographing the diaphanoscopic image, these optical systems may be provided separately.

As described above, in accordance with the invention, it is possible to measure the corneal shape with high accuracy while suppressing the effect of the reflected light from the iris.

What is claimed is:

1. A corneal shape measuring apparatus for measuring a corneal shape of an eye to be examined, the apparatus comprising:

index projecting means having a first projecting optical system for projecting a corneal shape measuring index onto a cornea of the eye;

index detecting means having a first imaging optical system for obtaining an image of an anterior eye segment including an image of the measuring index formed on the cornea;

arithmetic means for obtaining the corneal shape based on the obtained image of the measuring index; and input means for inputting, to the arithmetic means, information on a boundary position between a pupil and an iris of the eye, wherein the arithmetic means corrects information on the image of the measuring index based on the information on the boundary position thus inputted, and obtains the corneal shape based on the thus corrected information on the image of the measuring index.

2. The apparatus of claim 1, further comprising:

diaphanoscopic image obtaining means having an illuminating optical system for projecting a light onto a fundus of the eye, and illuminating the anterior eye segment with the light reflected from the fundus, and a second imaging optical system for obtaining a diaphanoscopic image of the anterior eye segment; and boundary position detecting means for detecting the boundary position between the pupil and the iris based on the diaphanoscopic image thus obtained, wherein the input means inputs information on the thus detected boundary position to the arithmetic means.

3. The apparatus of claim 2, wherein the second imaging optical system is used commonly as the first imaging optical system.

4. The apparatus of claim 2, further comprising:

ocular refractive power measuring means having a second projecting optical system for projecting a light onto the fundus of the eye, and light receiving optical system for receiving the light reflected from the fundus of the eye, wherein the illuminating optical system is used commonly as the second projecting optical system.

5. The apparatus of claim 1, wherein the arithmetic means divides luminance information on the image of the measuring index into a pupil region and an iris region based on the inputted boundary position information, obtains a luminance difference between the pupil region and the iris region, remove reflected light component of the iris region based on the thus obtained luminance difference to correct the luminance information on the image of the measuring index, and obtains the corneal shape based on the thus corrected luminance information.

6. The apparatus of claim 1, further comprising:

displaying means for displaying the image of the anterior eye segment thus obtained, wherein the input means inputs the boundary position between the pupil and the iris based on a display by the displaying means.

7. The apparatus of claim 1, wherein the index projecting means includes means for projecting, as the measuring index, a ring pattern index onto the cornea, and the arithmetic means detects an edge position of the obtained ring pattern index, and obtains a corneal curvature based on the detected edge position.

8. The apparatus of claim 7, wherein the first projecting optical system provided in the index projecting means includes:

a Placid plate in which light transmitting portions and light shielding portions are alternately arranged substantially concentrically; and a plurality of light sources for illuminating the Placid plate.

9. The apparatus of claim 8, wherein the light sources emits a light whose wavelength falls within red to infrared region.

10. A corneal shape measuring apparatus for measuring a corneal shape of an eye to be examined, the apparatus comprising:

image input means for inputting an image of an anterior eye segment including a corneal shape measuring index image formed on a cornea;

arithmetic means for obtaining the corneal shape based on the inputted measuring index image;

boundary position input means for inputting, to the arithmetic means, information on a boundary position between a pupil and an iris of the eye, wherein the arithmetic means corrects information on the measuring index image based on the inputted information on the boundary position, and obtains the corneal shape based on the corrected information on the measuring index image.

11. The apparatus of claim 10, further comprising:

diaphanoscopic image obtaining means having an illuminating optical system for projecting a light onto a fundus of the eye, and illuminating the anterior eye segment with the light reflected from the fundus, and an imaging optical system for obtaining a diaphanoscopic image of the anterior eye segment; and boundary position detecting means for detecting the boundary position between the pupil and the iris based on the diaphanoscopic image thus obtained, wherein the boundary position input means inputs information on the thus detected boundary position to the arithmetic means.

12. The apparatus of claim 11, further comprising:

ocular refractive power measuring means having a projecting optical system for projecting a light onto the fundus of the eye, and a light receiving optical system for receiving the light reflected from the fundus of the eye, wherein the illuminating optical system is used commonly as the projecting optical system.

13. The apparatus of claim 10, wherein the arithmetic means divides luminance information on the measuring index image into a pupil region and an iris region based on the inputted boundary position information, obtains a luminance difference between the pupil region and the iris region, remove reflected light component of the iris region based on the thus obtained luminance difference to correct the luminance information on the measuring index image, and obtains the corneal shape based on the thus corrected luminance information.

14. The apparatus of claim 10, further comprising:

displaying means for displaying the obtained image of the anterior eye segment, wherein the boundary position input means inputs the boundary position between the pupil and iris based on a display by the displaying means.

15. The apparatus of claim 10, wherein the image input means inputs the image of the anterior eye segment in which an image of a ring pattern index is formed as the measuring index on the cornea, and arithmetic means detects an edge position of the inputted image of the ring pattern index, and obtains a corneal curvature based on the detected edge position.

* * * * *